US012733959B2

(12) United States Patent
Refai et al.

(10) Patent No.: US 12,733,959 B2
(45) Date of Patent: Sep. 15, 2026

(54) ARTICULATING ROD ASSEMBLY

(71) Applicant: Refai Technologies, L.L.C., Atlanta, GA (US)

(72) Inventors: Daniel Refai, Atlanta, GA (US); Tyler Haskins, West Chester, PA (US)

(73) Assignee: Refai Technologies, L.L.C., Atlanta, GA (US)

( * ) Notice: Subject to any disclaimer, the term of this patent is extended or adjusted under 35 U.S.C. 154(b) by 64 days.

(21) Appl. No.: 18/434,191

(22) Filed: Feb. 6, 2024

(65) Prior Publication Data

US 2024/0173053 A1 May 30, 2024

Related U.S. Application Data

(63) Continuation of application No. 16/819,942, filed on Mar. 16, 2020, now Pat. No. 11,890,035, which is a continuation of application No. 15/664,709, filed on Jul. 31, 2017, now Pat. No. 10,588,668, which is a continuation of application No. 14/110,491, filed as application No. PCT/US2012/032312 on Apr. 5, 2012, now Pat. No. 9,717,535.

(60) Provisional application No. 61/473,342, filed on Apr. 8, 2011.

(51) Int. Cl.
*A61B 17/70* (2006.01)

(52) U.S. Cl.
CPC ........ *A61B 17/704* (2013.01); *A61B 17/7019* (2013.01); *A61B 17/7023* (2013.01); *A61B 17/705* (2013.01); *A61B 17/7055* (2013.01)

(58) Field of Classification Search
CPC .............. A61B 17/7049; A61B 17/705; A61B 17/7052; A61B 17/704; A61B 17/7019; A61B 17/7023; A61B 17/7055
See application file for complete search history.

(56) References Cited

U.S. PATENT DOCUMENTS

| | | | |
|---|---|---|---|
| 3,433,510 | A | 3/1969 | Hulterstrum |
| 5,800,435 | A | 9/1998 | Errico |
| 7,695,500 | B2 | 4/2010 | Markworth |
| 7,901,433 | B2 | 3/2011 | Forton |
| 7,909,852 | B2 | 3/2011 | Boomer |
| 8,568,459 | B2 | 10/2013 | Uribe |
| 8,690,923 | B2 | 4/2014 | Lynch |

(Continued)

FOREIGN PATENT DOCUMENTS

| | | |
|---|---|---|
| EP | 2158862 | 3/2010 |

*Primary Examiner* — Ellen C Hammond
(74) *Attorney, Agent, or Firm* — Heslin Rothenberg Farley & Mesiti P.C.; Jacquelyn A. Graff, Esq.

(57) ABSTRACT

An articulating assembly includes a first elongated element for attachment to a first anatomical region, and a second elongated element for attachment to a second anatomical region. In at least one embodiment, a coupling connects the first and second elongated elements. The coupling includes a moveable joint configured to allow polyaxial movement of the first elongated element with respect to the second elongated element. The assembly further includes a locking mechanism. The locking mechanism is operable in an unlocked condition to permit polyaxial movement of the first elongated element with respect to the second elongated element, and a locked condition to immobilize the movable joint and fix the position of the first elongated element with respect to the second elongated element.

19 Claims, 6 Drawing Sheets

(56) References Cited

U.S. PATENT DOCUMENTS

| | | | | |
|---|---|---|---|---|
| 8,870,922 | B2 | 10/2014 | Hammer | |
| 8,945,186 | B2 | 2/2015 | Walker | |
| 2005/0288669 | A1 | 12/2005 | Abdou | |
| 2007/0118121 | A1 | 5/2007 | Purcell | |
| 2008/0243186 | A1 | 10/2008 | Abdou | |
| 2009/0157120 | A1* | 6/2009 | Marino .............. | A61B 17/7049 606/278 |
| 2010/0049252 | A1* | 2/2010 | Smisson, III ...... | A61B 17/7043 606/264 |
| 2010/0234892 | A1* | 9/2010 | Mazda ............... | A61B 17/7056 606/276 |
| 2012/0078306 | A1 | 3/2012 | Lynch | |
| 2012/0226316 | A1 | 9/2012 | Dant | |

* cited by examiner 210b
210a
270

270
210a
210b 210b
270
210a 278
277
274b
270
274a
210a
210b
AP 276
272
274
277
210b
274b
210a
274
274a
272
276

278
275a
277
275
210b
274
272
210a
276

ML
278
274b
210b
270
274a
210a 310b
370
310a 310b
370
310a
374

370
310a
310b 374
310a
310b
372
376

310b
374
310a
AP
372
376

310b
310a
374
372
376

378
377
374
379
310b
375a
375
378a
310a
376
374a
374b
372
379a

ARTICULATING ROD ASSEMBLY

RELATED APPLICATIONS

This application is a continuation of U.S. application Ser. No. 16/819,942 filed Mar. 16, 2020, which will issue as U.S. Pat. No. 11,890,035 on Feb. 6, 2024, which is a continuation of U.S. application Ser. No. 15/664,709 filed Jul. 31, 2017, which issued as U.S. Pat. No. 10,588,668 on Mar. 17, 2020, which is a continuation of U.S. application Ser. No. 14/110,491 filed Apr. 3, 2014, which issued as U.S. Pat. No. 9,717,535 on Aug. 1, 2017, which is a National Phase application of International Application No. PCT/US2012/032312 filed Apr. 5, 2012 and published as WO 2012/138852 on Oct. 11, 2012, and which claims priority benefit under 35 U.S.C. § 119(e) of U.S. Provisional Application No. 61/473,342, filed Apr. 8, 2011, the contents of which are incorporated by reference herein in their entireties and for all purposes.

TECHNICAL FIELD

The present disclosure relates generally to surgical assemblies, and particularly to an articulating assembly that allows an elongated member to be angularly adjusted in multiple planes. The articulating assembly may be used, for example, to properly align fixation members with a patient's cervical vertebra and occipital region, or in a patient's lumbopelvic spine.

BACKGROUND

When performing posterior cervical stabilization, the surgeon typically places screws into the lateral mass of the cervical vertebral body followed by a titanium rod and set screws. This construct provides stabilization of the cervical spine to aid in fusion of one or more levels. Occasionally, one end section of the rod is anchored to a plate attached to the occipital region in a procedure called occipitocervical stabilization. In these constructs, the rod is characterized by two sections—a first section that extends over the cervical spine and a second section that connects to the occipital plate at an angle relative to the first section. One example of an occipitocervical fixation assembly 100 is shown in FIG. 1.

Fixation assembly 100 includes a pair of spinal rods 110. Each rod 110 is inserted into a series of screw assemblies 120 configured for anchoring into a vertebral body. Each screw assembly 120 includes a bone screw 130, a rod receiver 140, and a securing element 150 for locking one of the rods 110 into the rod receiver. Each rod 110 includes a first section **110*a* configured to extend over the cervical vertebrae and a second section 110*b* configured to attach to the patient's occipital region. The second sections 110*b* are anchored to an occipital plate 160 having two receivers 170 and two securing elements 180. Each rod 110 is bent to form an angle between its first section 110*a* and second section 110*b***.

In conventional occipitocervical fixation assemblies, the rod may be bent prior to placement to form the angle between the first and second sections. The pre-bent rod may be used to connect the screw or hook placed at C2 with the occipital plate. Alternatively, the screw or hook may be placed at C1 or C3. Because every patient has a different anatomy, one rod configuration will not suit all patients. Among other variables, the angle between the first and second rod sections will vary from patient to patient. Therefore, a pre-bent rod may not precisely match a patient's anatomy as the rod is placed. In many cases, the pre-bent rod requires further adjustment during placement, and must be bent intraoperatively.

Bending a rod prior to and during operation can be a time consuming and cumbersome process. In addition, bending the rod can create stress in the rod that decreases fatigue strength of the rod material. If fatigue strength is significantly reduced, the integrity of the rod can be compromised and pose a significant risk to the patient. The problems with rod bending are experienced not only with occipitocervical fixation assemblies, but are also experienced with lumbopelvic spine fixation assemblies, and other implant systems featuring elongated elements that must be manually configured to conform to specific spatial requirements.

SUMMARY

The drawbacks of conventional implant systems, and the practice of bending and shaping elongated elements, can be avoided with articulating assemblies in accordance with the invention.

Articulating assemblies in accordance with the invention may include an adjustable articulating assembly for implantation in a human or animal. The assembly may include a first elongated element for attachment to a first anatomical region, and a second elongated element for attachment to a second anatomical region. A coupling may connect the first and second elongated elements. The coupling may include a moveable joint configured to allow polyaxial movement of the first elongated element with respect to the second elongated element. The assembly may further include a locking mechanism. The locking mechanism may be operable in an unlocked condition to permit polyaxial movement of the first elongated element with respect to the second elongated element, and a locked condition to immobilize the movable joint and fix the position of the first elongated element with respect to the second elongated element.

BRIEF DESCRIPTION OF THE DRAWINGS

The foregoing summary and the following detailed description will be better understood in conjunction with the drawing figures, in which.

DETAILED DESCRIPTION OF EMBODIMENTS

Figure 1:
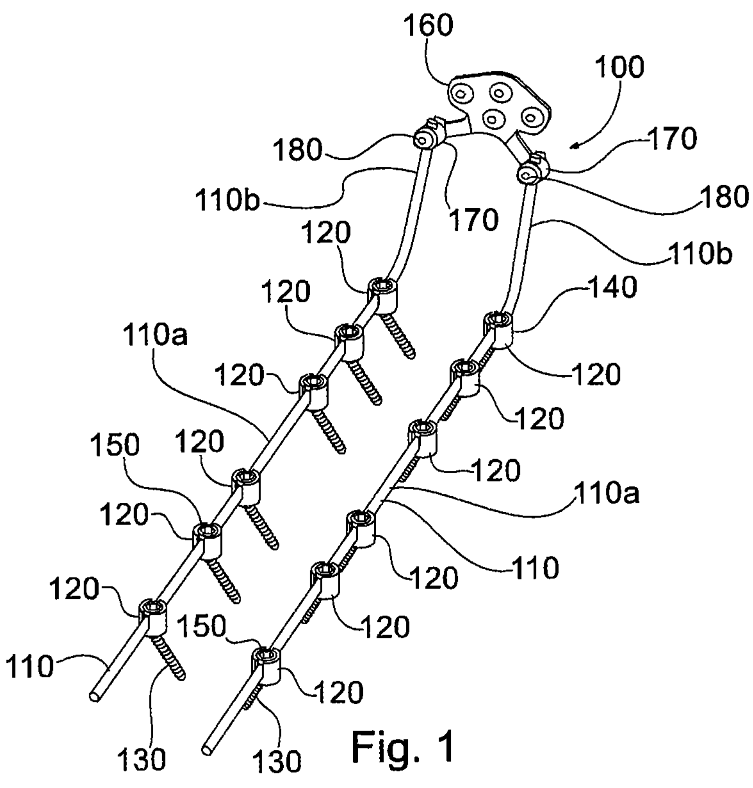
FIG. 1 is a perspective view of components of an occipitocervical stabilization system.
Figure 2:
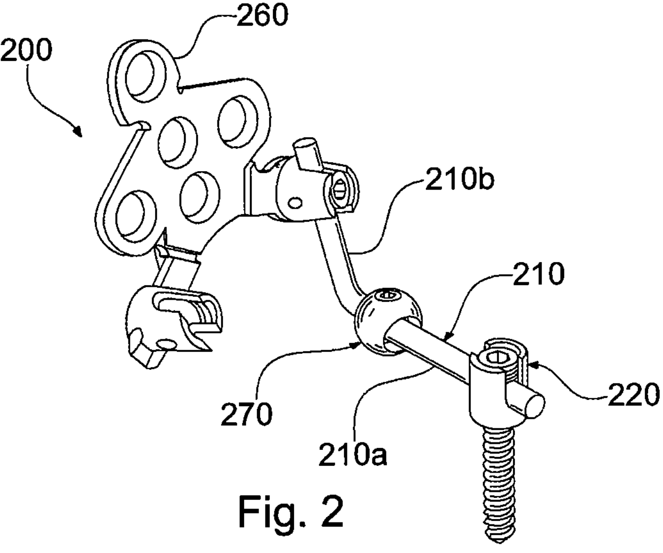
FIG. 2 is a truncated perspective view of an articulating fixation assembly in accordance with one embodiment.

Although the invention is illustrated and described herein with reference to specific embodiments, the invention is not intended to be limited to the embodiments shown. Various modifications may be made in the details within the scope and range of equivalents of the claims and without departing from the invention.

Assemblies in accordance with the invention may include an adjustable articulating assembly for implantation in a human or animal. The adjustable articulation assembly may include a first elongated element for attachment to a first anatomical region, and a second elongated element for attachment to a second anatomical region. The assembly may also include a coupling connecting the first elongated element with the second elongated element. The coupling may include a moveable joint configured to allow polyaxial movement of the first elongated element with respect to the second elongated element. The coupling may also include a locking mechanism. The locking mechanism may be operable in an unlocked condition to permit polyaxial movement of the first elongated element with respect to the second elongated element. The locking mechanism may also be operable in a locked condition to immobilize the movable joint and fix the position of the first elongated element with respect to the second elongated element.

The assembly may include a moveable joint that includes a ball and socket joint. The ball and socket joint may include a spherical end on at least one of the first elongated element and the second elongated element. The first elongated element may be movable through an angle of at least about 20° relative to the second elongated element.

The locking mechanism may include at least one screw. The screw may include a tapered wedge portion. The screw may directly engage one of the first and second elongated elements when the locking mechanism is in the locked condition.

The moveable joint may feature a hollow receptacle. The hollow receptacle may be generally spherical. Alternatively, the hollow receptacle may be generally cylindrical. The hollow receptacle may include at least one open end. The open end may form an enlarged opening that passes into the hollow receptacle. The enlarged opening may include a tapered edge that tapers outwardly. The hollow receptacle may include at least one annular seat. The annular seat projects inwardly into a socket in the hollow receptacle.

The at least one annular seat may form a constricted opening having a first diameter. One of the first and second elongated elements may include a ball end disposed in the hollow receptacle, the ball end having a second diameter larger than the first diameter. The ball end may be compressed against the seat when the locking mechanism is in the locked condition.

The first and second elongated elements may be associated with assemblies that are implanted in various areas of a human or animal. For example, the first and second elongated elements may be associated with rod implants. The first and second elongated elements may include sections of an occipital spine fusion rod. Alternatively, the first and second elongated elements may include sections of a lumbar spine fusion rod. This description will now discuss embodiments that feature rods, with the understanding that assemblies in accordance with the invention can be used with other elongated elements.

Applicants have developed an articulating fixation assembly that allows the rod's angle to be easily adjusted in multiple planes. Angular adjustment is done by moving an articulating joint between the first and second sections, as opposed to bending the rod. The articulating joint simplifies the task of adjusting the rod angle, and creates no stress in the rod material. By adjusting the rod angle in multiple planes, the rod can be adjusted to not only match the patient's anatomy, but also meet additional spatial requirements necessitated by other components of the assembly or instrumentation.

Referring now to FIGS. 2-10, an articulating fixation assembly 200 is shown in accordance with a first exemplary embodiment. Assembly 200 includes two rods 210, one of which is shown, and one of which is not shown for clarity. Rod 210 includes a first section 210*a*, a second section 210*b* and a coupling 270 that interconnects the first and second sections together. First section 210*a*, which is truncated for clarity, is secured to a screw assembly 220. Second section 210*b* is connected to an occipital plate 260. It will be understood that first section 210*a* may be longer and connect with multiple anchors, like hooks or additional screw assemblies. In addition, it will be understood that assembly 200 includes two rods 210 that may be configured identically or differently.

Figures 3, 4, 5, 6, 7, 8, 9:
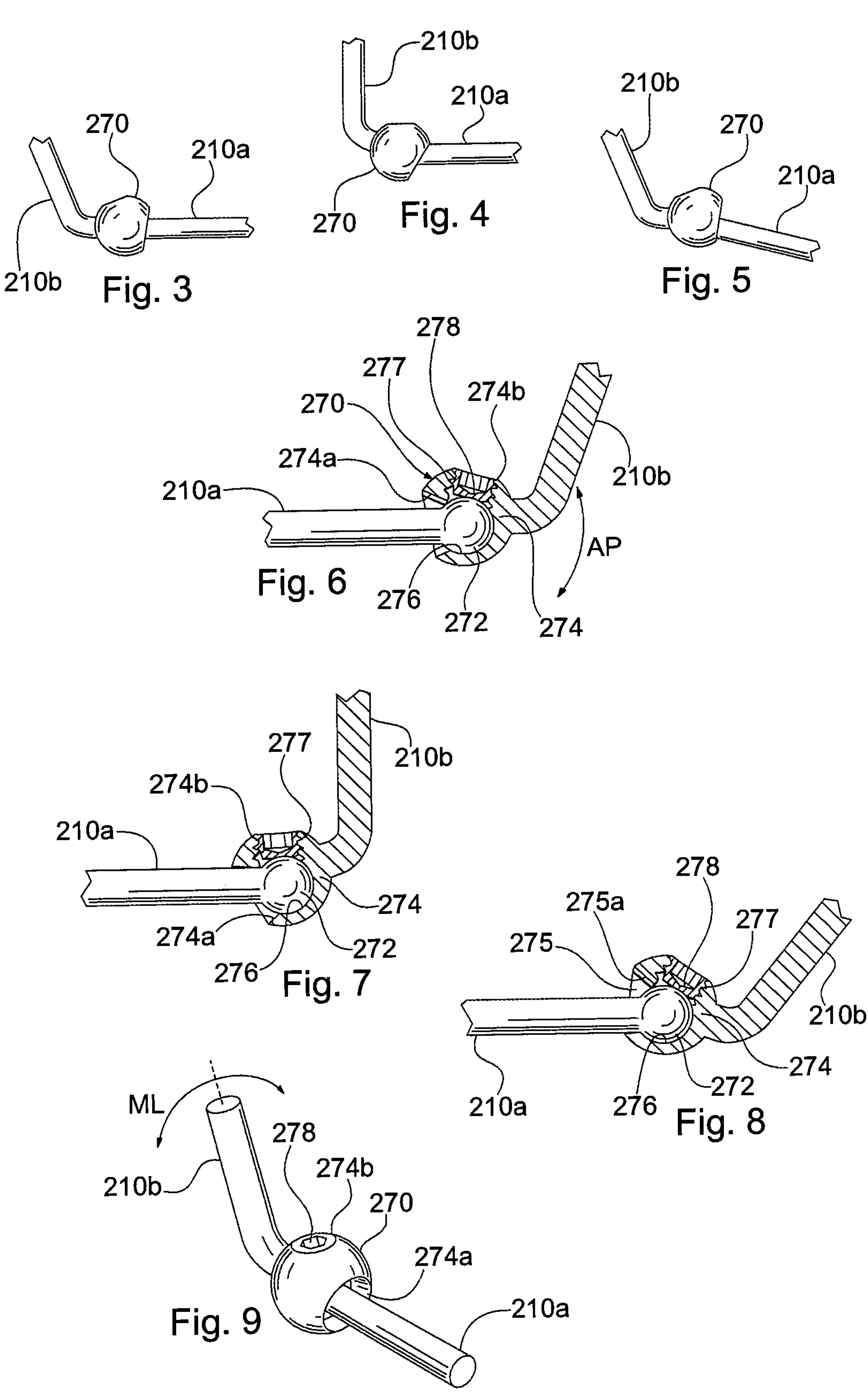
FIG. 3 is a truncated side view of components of the assembly in FIG. 2, shown in a first arrangement.
FIG. 4 is a truncated side view of components of the assembly in FIG. 2, shown in a second arrangement.
FIG. 5 is a truncated side view of components of the assembly in FIG. 2, shown in a third arrangement.
FIG. 6 is a truncated side view of components of the assembly in FIG. 2, shown in cross section in a fourth arrangement.
FIG. 7 is a truncated side view of components of the assembly in FIG. 2, shown in cross section in a fifth arrangement.
FIG. 8 is a truncated side view of components of the assembly in FIG. 2, shown in cross section in a sixth arrangement.
FIG. 9 is a truncated perspective view of components of the assembly in FIG. 2.
Figure 10:
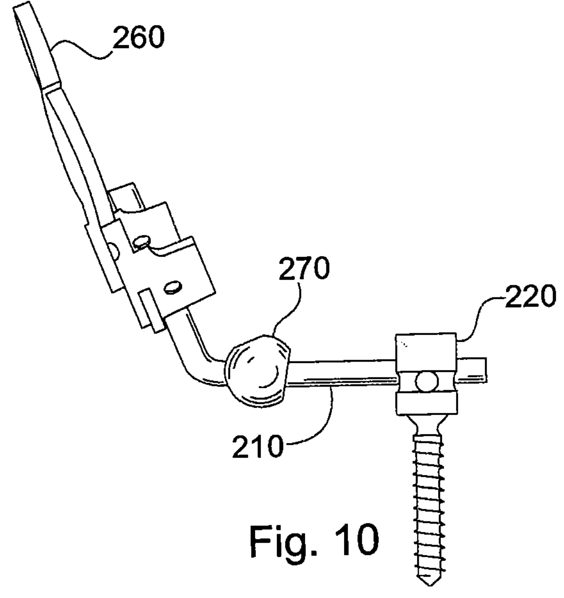
FIG. 10 is a truncated side view of components of the assembly in FIG. 2.
Figure 11:
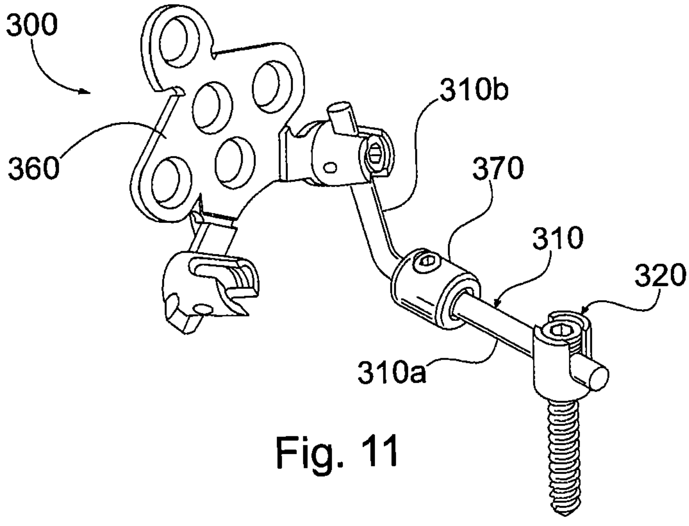
FIG. 11 is a truncated perspective view of an articulating fixation assembly in accordance with another embodiment.

FIGS. 6-8 illustrate how coupling 270 can be used to adjust the angulation between the first and second sections 210*a* and 210*b*. Coupling 270 is formed by a ball and socket joint. Specifically, coupling 270 includes a spherical ball end 272 on one end of first section 210*a* Coupling 270 further includes a receptacle 274 on one end of the second section 210*b* Receptacle 274 includes a rounded socket 276 adapted to receive ball end 272 inside the receptacle. Ball end 272 and socket 276 form the ball and socket joint that allows the first section 210*a* of rod 210 to move polyaxially with respect to the second section 210*b*. As used herein, the term "polyaxial" or "polyaxially" refers to the ability of a first element to pivot in multiple planes with respect to a second element to which the first element is coupled. First section 210*a* can move polyaxially with respect to second section

210*b*, and vice versa, so that the two sections can pivot in multiple planes with respect to one another. In this arrangement, second section 210*b* can pivot with respect to first section 210*a* in an anterior-posterior plane shown by arrows AP in FIG. 6, and a medial-lateral plane shown by arrows ML in FIG. 9.

Receptacle 274 has a generally spherical shape with two flattened sections 274*a* and 274*b*. Flattened section 274*a* lies adjacent to an enlarged opening 275 that passes through the receptacle 274 and into the socket 276. Enlarged opening 275 has a tapered edge 275*a* and a diameter that increases as the tapered edge extends outwardly and away from the center of receptacle 274. As such, tapered edge 275*a* forms a frustoconical surface around enlarged opening 275. Enlarged opening 275 and tapered edge 275*a* allow first section 210*a* to pivot polyaxially through a wide range of motion relative to second section 210*b*.

Flattened section 274*b* includes a passage 277 and a locking screw 278 in the passage. Locking screw 278 includes an external thread that engages an internal thread in passage 277. As such, locking screw 278 is movable in passage 277 by threading the screw into the passage and axially rotating the screw. Passage 277 extends into rounded socket 276. Locking screw 278 is movable in passage 277 between a locked position and an unlocked position. In the locked position, locking screw 278 is positioned in passage 277 and extends into rounded socket 276 to engage ball end 272. When locking screw 278 engages ball end 272 in the locked position, the locking screw compresses the ball end in the socket 276. In this compressed condition, frictional forces between ball end 272, screw 278 and the socket wall 276 immobilize the ball end and prevent it from pivoting, so that the first section 210*a* of rod 210 is locked in position relative to second section 210*b*. In the unlocked position, locking screw 278 is positioned in passage 277 out of contact with ball end 272, leaving the ball end free to move in socket 276. This allows first section 210*a* to pivot polyaxially relative to second section 210*b*.

FIGS. 11-20 illustrate an articulating fixation assembly 300 shown in accordance with a second exemplary embodiment. Assembly 300 includes two rods 310, one of which is shown, and one which is not shown for clarity. Rod 310 includes a first section 310*a*, a second section 310*b* and a coupling 370 that interconnects the first and second sections together. First section 310*a*, which is truncated for clarity, is secured to a screw assembly 320. Second section 310*b* is connected to an occipital plate 360. It will be understood that first section 310*a* may be longer and connect with multiple anchors, like hooks or additional screw assemblies. In addition, it will be understood that assembly 300 includes two rods 310 that may be configured identically or differently.

Figures 12, 13, 14, 15, 16, 17, 18:
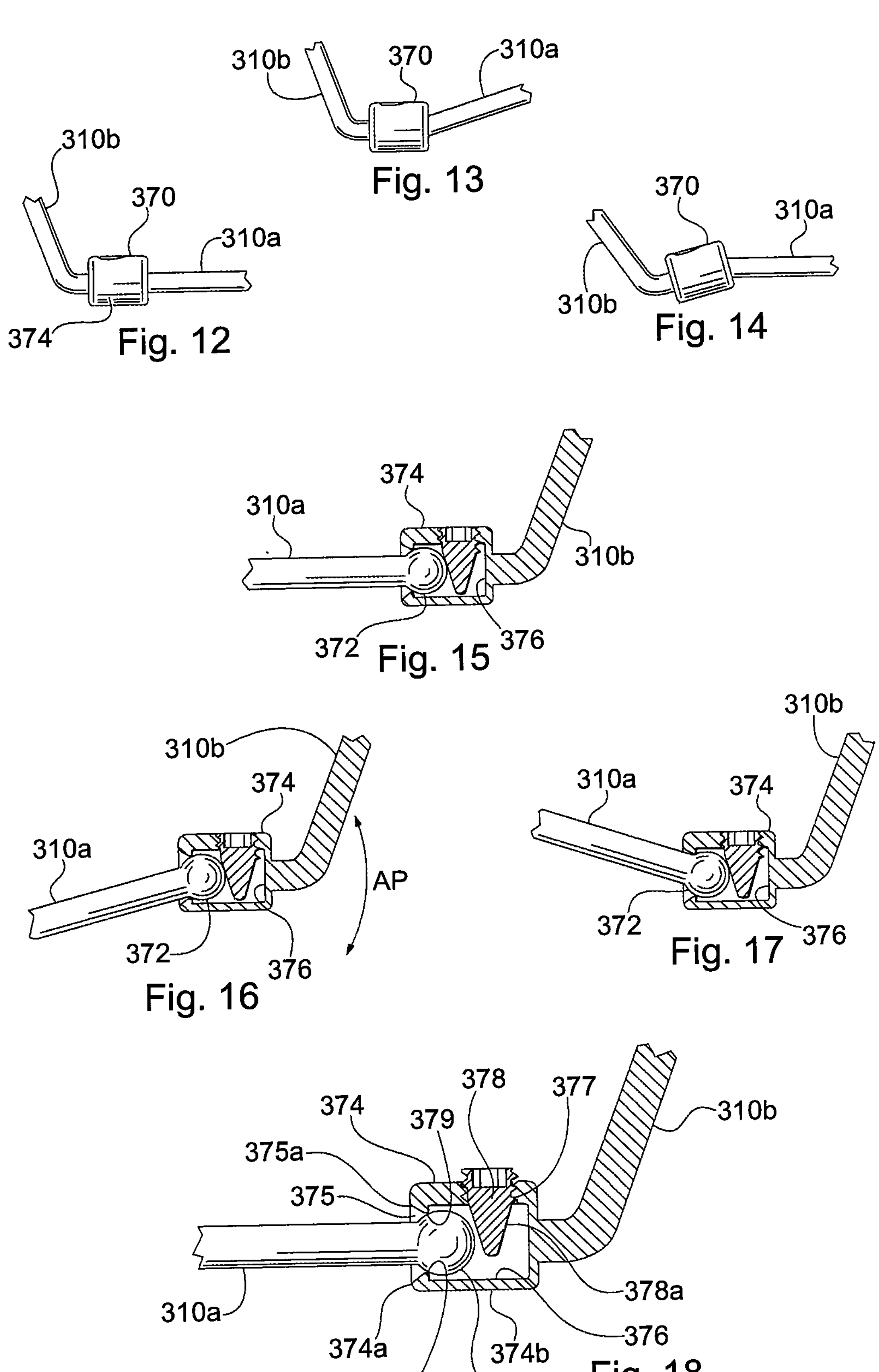
FIG. 12 is a truncated side view of components of the assembly in FIG. 11, shown in a first arrangement.
FIG. 13 is a truncated side view of components of the assembly in FIG. 11, shown in a second arrangement.
FIG. 14 is a truncated side view of components of the assembly in FIG. 11, shown in a third arrangement.
FIG. 15 is a truncated side view of components of the assembly in FIG. 11, shown in cross section in a first locked arrangement.
FIG. 16 is a truncated side view of components of the assembly in FIG. 11, shown in cross section in a second locked arrangement.
FIG. 17 is a truncated side view of components of the assembly in FIG. 11, shown in cross section in a third locked arrangement.
FIG. 18 is a side view of components of the assembly in FIG. 11, shown in cross section in an unlocked arrangement.
Figure 19:
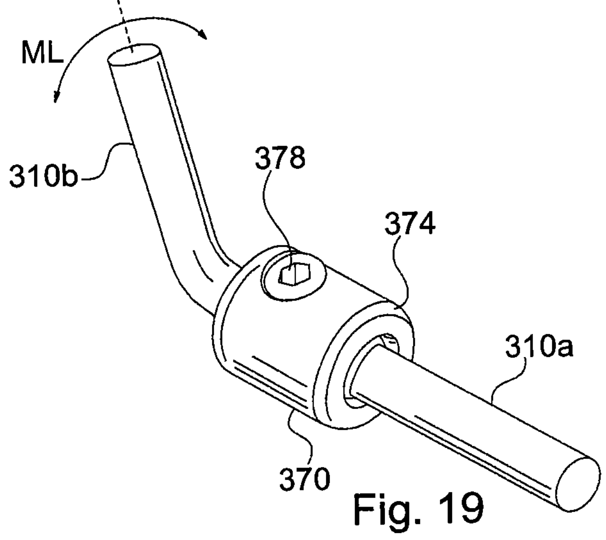
FIG. 19 is a truncated perspective view of components of the assembly in FIG. 11.
Figure 20:
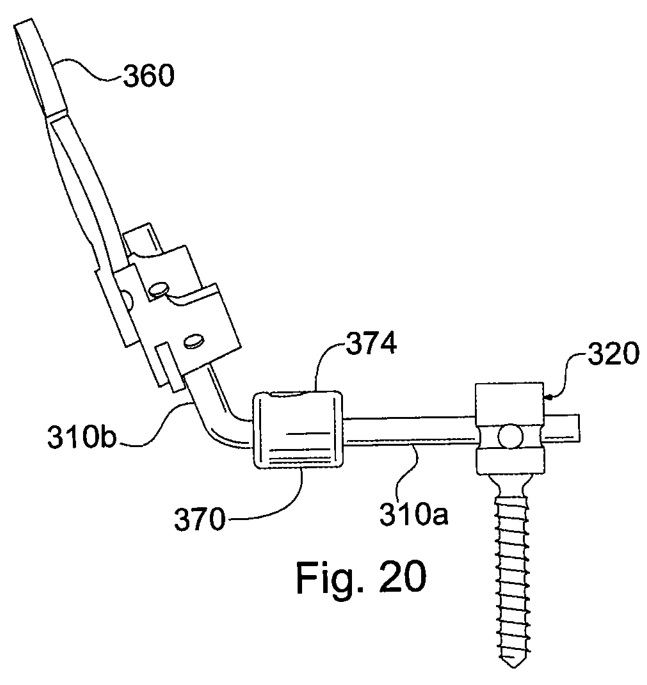
FIG. 20 is a truncated side view of the assembly in FIG. 11.

FIGS. 15-17 illustrate how coupling 370 can be used to adjust the angulation between the first and second sections 310*a* and 310*b*. Coupling 370 includes a spherical ball end 372 on one end of first section 310*a*. Coupling further includes a receptacle 374 on one end of the second section 310*b*. Receptacle 374 includes a cylindrical socket 376 adapted to receive ball end 372 inside the receptacle. Ball end 372 and socket 376 form the ball and socket joint that allows the first section 310*a* of rod 310 to move polyaxially with respect to the second section 310*b*. First section 310*a* and second section 310*b* can pivot in multiple planes with respect to one another. In this arrangement, second section 310*b* can pivot with respect to first section 310*a* in an anterior-posterior plane shown by arrows AP in FIG. 16, and a medial-lateral plane shown by arrows ML in FIG. 19.

Receptacle 374 has a generally cylindrical body 374*b* with one open end 374*a*. Open end 374*a* has an enlarged opening 375 that passes through the receptacle wall and into the socket 376. Enlarged opening 375 has a tapered edge 375*a* that tapers outwardly, allowing first section 310*a* to pivot polyaxially through a wide range of motion relative to second section 310*b*. Receptacle 374 further includes an annular seat 379 that projects radially inwardly into socket 376 as shown, just inside open end 374*a*. Seat 379 forms a constricted opening 379*a* having a diameter less than the diameter of ball end 372. In this arrangement, seat 379 prevents ball end 372 from exiting socket 376. Ball end 372 rests against seat 379 is slidable engagement, while being captively contained in socket 376.

Body 374*b* includes a passage 377 that connects with socket 376. A locking screw 378 is contained in the passage. Locking screw 378 includes an external thread that engages an internal thread in passage 377. As such, locking screw 378 is movable in passage 377 by threading the screw into the passage and axially rotating the screw. Locking screw 378 also includes a tapered shaft or wedge portion 378*a* that extends into socket 376.

Locking screw 378 is movable in passage 377 between a locked position and an unlocked position. In the locked position, wedge portion 378*a* of locking screw 378 extends into socket 376 and engages ball end 372. When locking screw 378 engages ball end 372 in the locked position, the locking screw compresses or wedges the ball end against seat 379, trapping the ball end between the wedge portion 378*a* and seat. In this trapped condition, frictional forces between ball end 372 and seat 379, and frictional forces between the ball end and wedge portion 378*a*, immobilize the ball end and prevent it from pivoting relative to socket 376. As such, first section 310*a* of rod 310 is locked in position relative to second section 310*b*. In the unlocked position, locking screw 378 is positioned in passage 377 with wedge portion 378*a* out of contact with ball end 372. This leaves ball end 372 free to move in socket 376, so that first section 310*a* can pivot polyaxially relative to second section 310*b*. FIGS. 15-17 show three different arrangements, each in a locked condition. FIG. 18 shows an arrangement in an unlocked condition.

The embodiments described thus far provide the benefit of a smooth articulating connection between first and second elongated elements. The connection allows multi-planar rotation that permits angular adjustment of the rod sections not only in the anterior-posterior plane but also the medial-lateral direction. Preferably, the connections in either embodiment provide about 20° of motion in each allowable direction (40° total through a given plane). A smaller or larger range of motion in one or more directions may be desirable in certain cases, and are therefore also contemplated. For example, the connections may permit a maximum of about 10° of motion in any allowable direction, or a maximum of about 15° of motion in any allowable direction. Or, the connections may permit a maximum of about 25° of motion in any allowable direction, or a maximum of about 30° of motion in any allowable direction.

The range of motion for a specific coupling may be controlled by the size and shape of the openings in the receptacles, through which the rod sections extend. For example, the size and shape of opening 375 may be customized to permit different ranges of motion in different planes. Where it is desired to have a larger range of motion in one plane, and a smaller range of motion in another plane, the opening through which the rod section extends may be elliptical in shape, with the major axis (or widest dimension)

of the elliptical opening aligned with the plane to receive the largest range of motion. Various openings having symmetrical and asymmetrical shapes may be used to control the range of pivot motion of the rod sections.

The embodiments that have been described thus far provide examples of articulating assemblies that permit angulation of rod sections in multiple planes. The foregoing examples do not represent the only possible arrangements that are contemplated. The features of one embodiment may be added to or substituted for features in another embodiment. Numerous variations, changes and substitutions will occur to those skilled in the art without departing from the principles described herein.

For example, an articulating rod assembly may include a receptacle with two or more locking elements that are advanced into the socket to lock the ball end in a locking position. The locking elements may be set screws with or without tapered wedge portions that engage the ball end. Alternatively, the locking elements can be non-threaded elements, such as a simple shim which is physically pushed into the socket against the ball end to prevent the ball end from pivoting in the socket. The locking elements may be removable from the receptacle, or captively contained in the wall of the receptacle.

Figure 21:
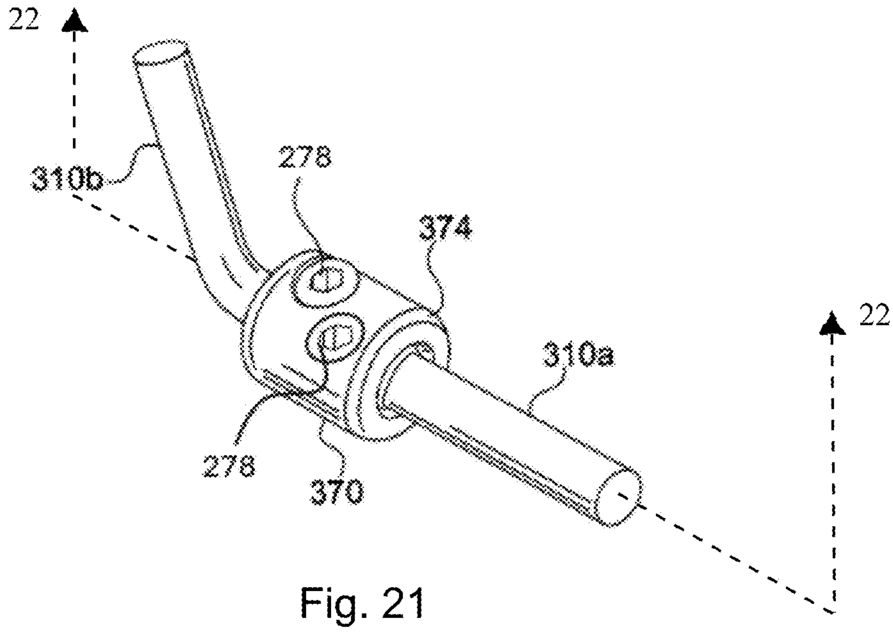
FIG. 21 is a truncated perspective view of another articulating fixation assembly, in accordance with an aspect of the present disclosure.
Figure 22:
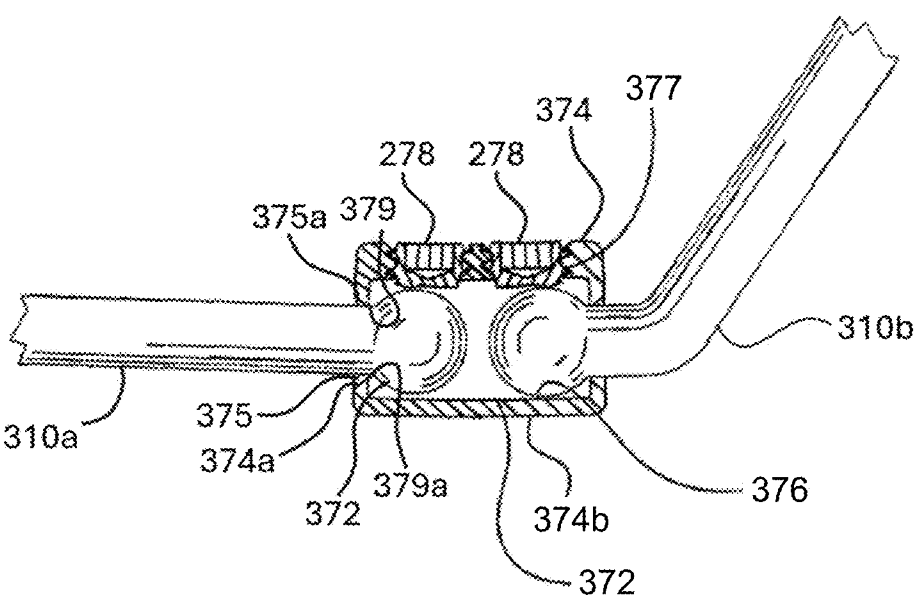
FIG. 22 is a cross-sectional view of the articulating fixation assembly of FIG. 21 taken along line 22-22, in accordance with an aspect of the present disclosure.

Articulating rod assemblies in accordance with the invention may also include multiple ball and socket joints within a single coupling, as shown in FIGS. 21-22. In one embodiment, the coupling is a cylindrical coupling with a spherical socket at each end. Each rod section includes a ball end, like first elongated element 310*a* in FIG. 15. Each ball end is disposed in one of the sockets, forming two ball and socket joints positioned at opposite ends of the cylindrical coupling. The ball and socket joints allow both rod sections to move polyaxially with respect to the cylindrical coupling, and to one another. A pair of locking mechanisms, such as set screws, extend through a wall of the cylindrical coupling. Each set screw is used to lock and unlock one of the ball and socket joints.

The receptacles may have various inner and outer geometries. Moreover, the receptacles may include one or more finger tabs or other external features that allow a surgeon to easily grip and pivot the coupling. The body of the receptacle and rods may include markings or indicia to assist the surgeon in monitoring, measuring or approximating the angular adjustments being made between the rod sections.

While the embodiments presented thus far are described in use with occipitocervical fixation assemblies, articulating assemblies in accordance with the invention may be used in a variety of applications. For example, an articulating assembly can be used to interconnect first and second rod sections that are implanted in the lumbar region of the spine. The first and second rod sections may be arranged in an offset configuration, with the articulating coupling providing the desired offset between the rod sections.

Articulation assemblies in accordance with the invention can also be used in a rod to rod connector construct. The articulating assembly can connect an existing fusion construct with another, to treat scoliosis or adjacent segment disease. A new rod fixation system can be connected to an existing rod using the articulating assembly.

Articulating assemblies in accordance with the invention may also be used in a variety of applications outside of spine surgery, including any applications where elongated members are connected to one another, or to other structures. It should be understood that assemblies in accordance with the invention need not be used with rods, as noted above. Assemblies in accordance with the invention may feature elongated elements in the form of elongated plates, shafts, or any type of elongated body member.

All such variations are contemplated as part of this disclosure and covered by the appended claims.

The invention claimed is:

1. An adjustable articulating spinal rod assembly, the assembly comprising:

- a first elongated element for attachment to a first anatomical region, wherein the first elongated element comprises:
  - a first enlarged end at an end of the first elongated element;
- a second elongated element for attachment to a second anatomical region, wherein the second elongated element comprises:
  - a second enlarged end at an end of the second elongated element; and
- at least one coupling member connecting the first elongated element with the second elongated element, the at least one coupling member comprising:
  - a body having a first opening, a second opening, and two third openings, wherein the first opening is at a first end of the body, the second opening is at a second end of the body, and the two third openings are positioned on a side of the body between the first end and the second end and extends through the body into at least one socket; and
  - two locking mechanisms received within the two third openings;
  - wherein the body has a cylindrical shape and the first enlarged end is positioned on a side opposite the second enlarged end of the body;
  - wherein the first elongated element extends through the first opening to position the first enlarged end in the at least one socket;
  - wherein the second elongated element extends through the second opening to position the second enlarged end in the at least one socket; and
  - wherein the two locking mechanisms are inserted into the two third openings to engage a portion of at least one of the first enlarged end of the first elongated element and a portion of the second enlarged end of the second elongated element.

2. The assembly of claim 1, wherein the first enlarged end of the first elongated element is arcuate shaped.

3. The assembly of claim 1, wherein the socket of the at least one socket at the first end of the body and the first end of the first elongated element is configured as a ball and socket joint and, wherein the socket of the at least one socket at the second end of the body and the first end of the second elongated element is configured as a ball and socket joint.

4. The assembly of claim 1, wherein the two locking mechanisms are threaded set screws, and wherein each threaded set screw directly engages at least one of the first enlarged end and the second enlarged end.

5. The assembly of claim 4, wherein at least one of the two threaded set screws comprises a tapered wedge portion, wherein the tapered wedge portion of the threaded set screws pressingly engage at least one of the first enlarged end of the first elongated element and the second enlarged end of the second elongated element when at least one of the two locking mechanisms are in a locked position.

6. The assembly of claim 1, wherein the two third openings of the body are threaded on at least a portion between an outer surface of the body into the at least one socket.

7. The assembly of claim 6, wherein the threads of the two third openings are configured to engage two threaded set screws.

8. The assembly of claim 1, wherein the body comprises an outer surface and is generally cylindrically shaped and wherein the outer surface has one or more tabs extending outward from the outer surface.

9. The assembly of claim 1, wherein the body comprises an outer surface and is generally cylindrically shaped and wherein the outer surface has at least one marking or indicia for measuring angular adjustments between the first elongated element and the second elongated element.

10. The assembly of claim 1, further comprising a third elongated element and a fourth elongated element, wherein the third elongated element and the fourth elongated element are parallel to the first elongated element and second elongated element when the assembly is implanted in a spine.

11. The assembly of claim 10, wherein the first elongated element and the second elongated element further comprises at least one screw assembly, wherein the at least one screw assembly comprises:

a bone screw;

a rod receiver; and a securing element, wherein the rod receiver has a channel through which at least one of the first elongated element and the second elongated element pass.

12. The assembly of claim 11, wherein the at least one screw assembly is moveable along a length of the first elongated element, the second elongated element, the third elongated element and the fourth elongated element to attach the first elongated element to the first anatomical region, to attach the second elongated element to the second anatomical region, to attach the third elongated element to a third anatomical region and to attach the fourth elongated element to a fourth anatomical region.

13. The assembly of claim 10, wherein the first elongated element and the third elongated element are connected to a plate member, wherein the plate member is configured to be attached to a human skull.

14. The assembly of claim 1, wherein a first of the two third openings receives a first locking mechanism of the two locking mechanisms to engage at least a portion of the first enlarged end of the first elongated element, and wherein a second of the two third openings receives a second locking mechanism of the two locking mechanisms to engage at least a portion of the second enlarged end of the second elongated element.

15. The assembly of claim 1, wherein the first opening is at an opposite end of the body from the second opening.

16. The assembly of claim 1, wherein at least one of the first opening and the second opening are generally elliptical.

17. The assembly of claim 1, wherein the two locking mechanisms are operable in an unlocked condition to allow polyaxial movement of the first elongated element and the second elongated element with respect to the at least one coupling member and wherein the two locking mechanisms are operable in a locked condition to fix the position of the first elongated element and the second elongated element with respect to the at least one coupling member.

18. The assembly of claim 1, wherein the body of the at least one coupling member comprises:

a cylindrical portion;

a first socket at a first end of the cylindrical portion, wherein the first enlarged end of the first elongated element is received within the first socket; and a second socket at a second end of the cylindrical portion, wherein the second enlarged end of the second elongated element is received within the second socket.

19. The assembly of claim 18, wherein the first socket comprises one third opening of the two third openings for receiving a first locking mechanism of the two locking mechanisms and wherein the second socket comprises another third opening of the two third openings for receiving a second locking mechanism of the two locking mechanisms.

* * * * *